United States Patent [19]

Helmling et al.

[11] Patent Number: 5,532,362
[45] Date of Patent: Jul. 2, 1996

[54] FIBER-REACTIVE TRIPHENODIOXAZINE DYES

[75] Inventors: Walter Helmling, Niedernhausen, Germany; David Brunetti, Harrisville, R.I.; Uwe Reiher, Hofheim, Germany

[73] Assignee: Hoechst Celanese Corporation, Somerville, N.J.

[21] Appl. No.: 450,965

[22] Filed: May 25, 1995

[51] Int. Cl.⁶ .................................................. C07D 498/04
[52] U.S. Cl. .................................... 544/77; 544/76
[58] Field of Search ........................... 544/76, 77

[56] References Cited

U.S. PATENT DOCUMENTS

| | | | |
|---|---|---|---|
| 3,022,298 | 2/1962 | Mory et al. | 544/77 |
| 4,604,489 | 8/1986 | Jager | 544/76 |
| 4,782,150 | 11/1988 | Springer et al. | 544/77 |
| 5,378,817 | 1/1995 | Bootz et al. | 534/618 |

*Primary Examiner*—Philip R. Datlow
*Attorney, Agent, or Firm*—Hugh C. Crall

[57] ABSTRACT

The present invention is directed to a dioxazine dye which provides brilliant reddish blue dyeings possessing superior fastness properties and high tinctorial strength.

6 Claims, No Drawings

FIBER-REACTIVE TRIPHENODIOXAZINE DYES

BACKGROUND OF THE INVENTION

1. Technical Field

This invention is directed to new fiber reactive triphenodioxazine dye.

2. Background

Anthraquinone based fiber reactive dyes have been the predominant dye used in the coloring of cotton fabrics in bright blue colors. This dominance of the anthraquinone dyes has been threatened over the past decade or so by the increasing use of dyes based upon the triphenodioxazine chromophore.

In the EPO 385,120 and the U.S. Pat. No. 4,604,459 fiber-reactive triphenodioxazines are described, which contain a fluoro-s-triazinyl or chloro-s-triazinyl group in conjunction with a vinylsulfone group as the reactive moiety. However, this type of triphenodioxazine s has disadvantages such as a very high affinity to the cellulose fiber. This high affinity causes problems in the use of these dyes, because the hydrolyzed dyestuff can not be easily washed off after the dyeing process and can stain other fabric during the washing process especially undyed fabric.

Surprisingly, it was found that a new class of fiber-reactive triphenodioxazine dyes provide superior wash off property and provide excellent light and chlorine fastness.

In addition, the dyes of the invention have a very high tinctorial strength and give brilliant reddish blue dyeings with high fixation.

SUMMARY OF THE INVENTION

The invention is that of a new triphenodioxazine dye of the formula:

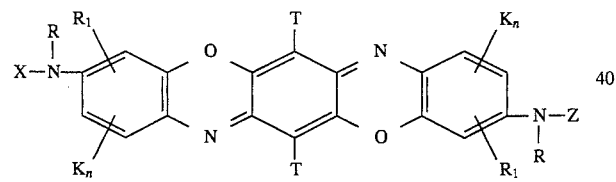

wherein:

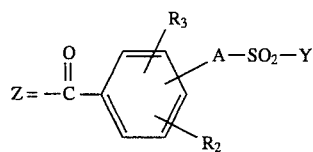

and wherein:

A is a covalent bond or a substituted or unsubstituted arylene, alkylene or arylene-alkylene group where the alkylene moiety may be optionally interrupted by a hetero atom preferably selected from O, S and N;

Y is the vinyl group or the β-chloroethyl group and;

X is selected from H or Z;

K is independently selected from $SO_3H$ and COOH;

R and $R_1$ are independently selected from hydrogen and substituted or unsubstituted alkyl of 1 to 6 carbons;

$R_2$ and $R_3$ are independently selected from hydrogen and substituted or unsubstituted alkyl or alkoxy of 1 to 6 carbons;

T is independently selected from hydrogen, Cl, Br, a substituted or unsubstituted $C_1$ to $C_6$ alkyl, $C_1$ to $C_6$ alkoxy, phenyl or phenoxy; and n is independently selected from 0, 1 or 2.

The dyes of the above formula provide dyeing on cotton substrates having a bright reddish blue color with superior fastness properties of high tinctorial strength. The dyes of the invention may also be used in the dyeing of other textiles containing amido and/or hydroxyl groups; exemplary materials include regenerated cellulose, synthetic polyamides, wool, silk polyurethane fibers and blends of such fibers. The dyes of the invention may be applied by the standard methods for printing and dyeing textiles with fiber reactive dyes.

DESCRIPTION OF THE PREFERRED EMBODIMENTS

The invention relates to new triphenodioxazine reactive dyestuffs of the formula:

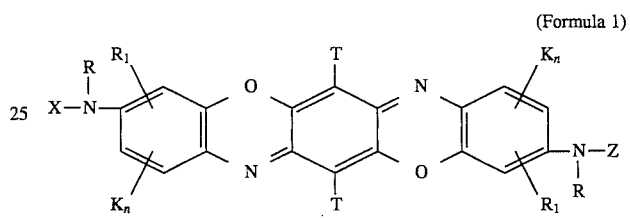

(Formula 1)

wherein:

R and $R_1$ are independently selected from H or a substituted or unsubstituted alkyl, preferably hydrogen or a substituted or unsubstituted $C_1$-$C_6$ alkyl, and most preferably hydrogen and a substituted or unsubstituted $C_1$-$C_4$ alkyl;

T is independently selected from H, Cl, Br, a substituted or unsubstituted $C_1$-$C_4$ alkyl, $C_1$-$C_4$ alkoxy, phenyl or phenoxy;

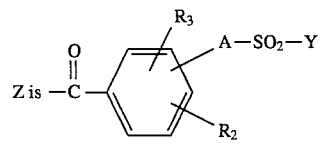

wherein:

$R_2$ and $R_3$ are selected from hydrogen or a substituted or unsubstituted $C_1$ to $C_6$ alkyl or $C_1$ to $C_6$ alkoxy; preferably hydrogen or a substituted or unsubstituted $C_1$ to $C_4$ alkyl or $C_1$ to $C_4$ alkoxy.

K is independently selected from $SO_3H$ and COOH; preferably $SO_3H$;

n is independently selected from 0, 1, 2; preferably 1, 2;

A is a covalent bond or a substituted or unsubstituted arylene, or alkylene or arylene-alkylene group wherein the alkylene group may be optionally interrupted by a hetero atom preferably selected from O, S and N; A is preferably a covalent bond or a substituted or unsubstituted $C_1$ to $C_6$ alkylene group, wherein said alkylene moiety may be optionally interrupted by a hetero atom preferably selected from O, N and S; and Y is the vinyl group or the β-chloroethyl group.

The term "arylene-alkylene" group as used in this specification and the claims is intended to mean a phenylene or naphthylene group bonded to one or more alkylene group, e.g. the following illustrations or their isomers:

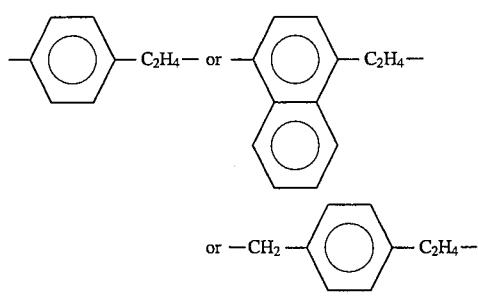 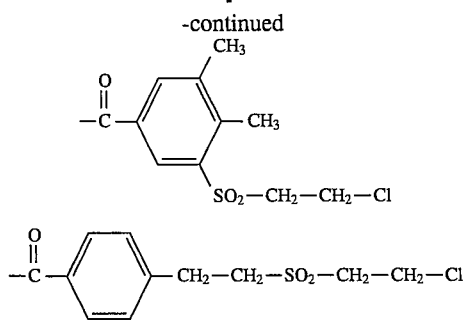

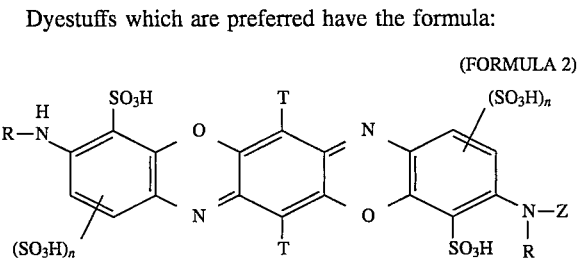

Examples of R and $R_1$ are: hydrogen, $CH_3$, $C_2H_5$, n-$C_3H_7$, n-$C_4H_9$, n-$C_6H_{16}$, which may be optionally substituted by OH, $OCH_3$, $C_2H_5$, COOH, $SO_3H$, $OSO_3H$, Cl.

Examples of $R_2$ and $R_3$ are: hydrogen, $CH_3$, $C_2H_5$, n-$C_3H_7$, $OCH_3$, $OC_2H_5$, which may be optionally substituted by OH, $OCH_3$, $OC_2H_5$, COOH, $SO_3H$, $OSO_3H$, Cl.

Examples of the substituents in substituted alkyl, alkoxy, phenyl, arylene, alkylene, arylene-alkylene and phenoxy groups are OH, $OCH_3$, $OC_2H_5$, COOH, $SO_3H$, $OSO_3H$, CN, Cl, Br or F; preferably $OCH_3$, $OC_2H_5$, COOH, $SO_3H$, $OSO_3H$, $C_1$-$C_4$ alkyl and $C_1$-$C4$ alkoxy.

Preferably R and $R_1$ are hydrogen; $R_2$ and $R_3$ are preferably hydrogen, $CH_3$ or $OCH_3$ and A is preferably a covalent bond or a $CH_2$ group.

Exemplary type "Z" groups are:

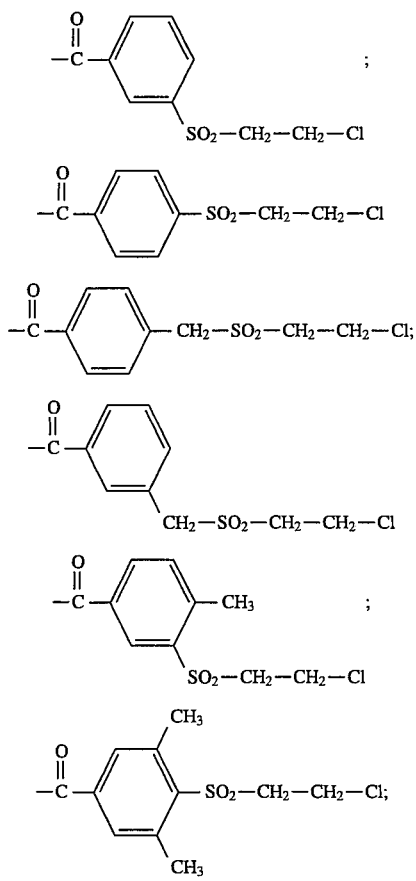

Dyestuffs which are preferred have the formula:

(FORMULA 2)

wherein T and R are as previously defined and n is 0, 1.
The moiety Z may be represented by the formula:

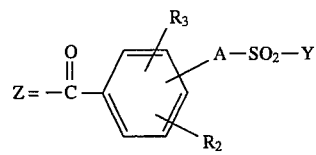

wherein A is independently selected from a covalent bond or a $C_1$- $C_2$ alkylene group; preferably a $C_2$ alkylene.
Y is defined above and $R_2$, $R_3$ are selected from H, $CH_3$, $OCH_3$.

Preferred dyestuffs of Formula 1 are those in which T is Cl, n is 1, X is H or Z, K is $SO_3H$, or COOH, $R_1$ is H, R is H and

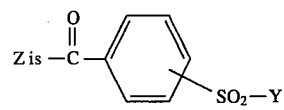

wherein Y is the vinyl or β-chloroethyl group and the benzene ring of said Z moiety can contain further substituents; examples of such substituents are: $CH_3$, $OCH_3$.

The invention also relates to a process for preparing the dyestuffs of the Formula 1 wherein the moiety X is hydrogen. This process is characterized in that about 1 mole of a triphenodioxazine dyestuff of the Formula 3:

(FORMULA 3)

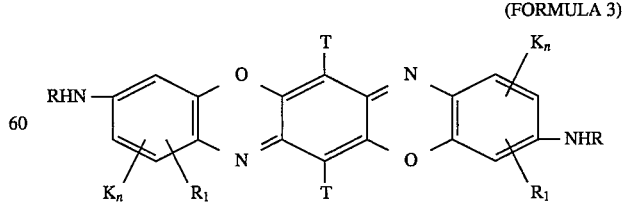

preferably in the form of the corresponding lithium salts is condensed with about 1–3 moles of the acid chloride—Z—Cl with elimination of 1 mole hydrochloric acid, preferably using basic lithium compounds such as lithium hydroxide or lithium carbonate as acid acceptors, to give the dyestuff of Formula 1.

Examples of the acid chloride—Z—Cl are the chloro adduct of the above defined radical—Z.

The acid chlorides Z—Cl are preferably best condensed with the dye of Formula 3 at temperatures of 0°–60° C., preferably 5°–40° C.; at pH 2–8 preferably 3–7, in an aqueous or aqueous-organic medium.

The preparation of compounds of the Formula 3 is effected by methods known to those skilled in the art by condensing 1-4-benzoquinones of the formula:

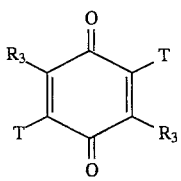
(FORMULA 4)

wherein

T has the above mentioned meaning and $R_3$ is independently selected from H, Cl, Br, a substituted or unsubstituted alkyl, a substituted or unsubstituted alkoxy or phenoxy, with diaminobenzenes of the formula:

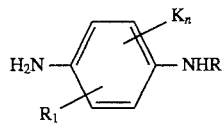
(FORMULA 5)

wherein R, $R_1$, K and n have the above mentioned meaning, to give a compound of the formula:

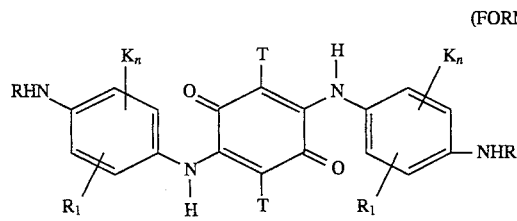
(FORMULA 6)

and subsequently cyclizing the diaminobenzene or dianilino compound 6 to give the basic dioxazine dyestuff of Formula 3.

The benzoquinones of the Formula 4 are preferably condensed with a diaminobenzenes of Formula 5 at temperatures of 0°–80° C., preferably 50°–70° C., at pH 2–10, preferably pH 5–7, in an aqueous or aqueous-organic reaction medium in the presence of alkaline condensing agents. It is also possible to work in a purely organic reaction medium in the presence of acid-binding agents. The condensation products of the Formula 6 can be precipitated by salting out or by acidification.

Exemplary reaction media are water, methanol, ethanol, and nitrobenzene. Exemplary acid-binding agents are sodium bicarbonate, sodium carbonate, sodium acetate, potassium acetate, sodium hydroxide, potassium hydroxide, sodium phosphates and sodium borate.

Examples of suitable diaminobenzenes of the Formula 8 are as follows: 1,4 -Diaminobenzene-2-sulfonic acid, 1,4-Diaminobenzene-2-carboxy acid, 1-Amino-4 -N-methylaminobenzene-3-sulfonic acid, 1-Amino-4-N-ethylaminobenzene-3-sulfonic acid, 1,4-Diamino-2-methoxybenzene-5-sulfonic acid, 1,4-Diamino-2-methylbenzene-5-sulfonic acid, 1,4-Diaminobenzene-2,5-disulfonic acid, 1,4-Diaminobenzene-2,5-dicarboxy acid, 1,4-Diamino-2-carboxybenzene-5-sulfonic acid, and 1,4-Diaminobenzene-2,6-disulfonic acid.

The cyclization of the dianilino compounds of the Formula 6 can be effected by methods known to those skilled in the art; see e.g., U.S. Pat. No. 4,604,459 and A. H. M. Renfrew, J. Soc. Dyers Colour. 105 (1989) 262–4, GB Patent No. 1,589,915 in particular, at temperatures of 10°–80° C. in oleum having an $SO_3$ contents of 1–50%, optionally in the presence of oxidizing agents such as potassium peroxodisulphate, ammonium peroxodisulphate and organic peroxides. In general, oleum having an $SO_3$ content of 5–30% is used in an amount of about 5–15 parts by weight per part by weight of the compound of Formula 10. Under the reactive conditions for cyclization in oleum it is possible to sulfonate aliphatic OH groups and sulfonate aromatic rings present in the dianilino compounds of the Formula 6; therefore milder conditions must be used if undesired sulfonation is encountered.

The new dyestuffs of the invention give bright reddish blue dyeings on cellulose and natural or synthetic polyamide materials. They are distinguished by high tinctorial strength. As water-soluble reactive dyestuffs, the new dyestuffs are preferably of interest for the dyeing of hydroxyl- and amido-containing textile materials, in particular materials in natural and regenerated cellulose and synthetic polyamide and polyurethane fibers, wool and silk.

These materials may be dyed or printed using the methods which are commonly known and customary in industry for water-soluble reactive dyestuffs to give light- and wet-fast blue dyeings and prints.

The temperatures in the Examples are given in ° C . The formulae of water-soluble reactive dyestuffs in the description and in the Examples are shown in the free acid form. In general, the dyestuffs are isolated and used in the form of their alkali metal salts, in particular in the form of the lithium, sodium or potassium salts. The preferred form of the fiber-reactive moiety Y is the β-chloroethyl group and the formulas that follow show Z in that form. It will be readily apparent to those skilled in the art that the equivalent vinyl group may be used.

It will also be apparent to the skilled worker that the reaction mixture may be a mixture of fiber reactive moieties and depending on the reaction conditions e.g. up to 40% of the vinyl moiety and up to about 5% of the non-reactive hydroxy moiety may be formed and up to 30% of the bisacylated product where X is Z in Formula 1.

EXAMPLE 1

13.6 parts of 2,9-diamino-6,13-dichlorotriphenodioxazine-1,8-disulfonic acid is suspended in 200 parts of water and brought to pH 7.0 by using an aqueous solution of 5% LiOH. The reaction mixture is stirred for one hour. The pH is adjusted with hydrochloric acid to pH 4.5 and 20 parts of 3-(β-chloroethylsulfonyl)-benzoylchloride dissolved in 100 parts of methylene chloride is added during 2 hours. The pH of the reaction is maintained between 4–6 using an aqueous solution of 5% LiOH. After stirring for 6 hours at room temperature the reaction is completed. High performance liquid chromatography can be used to indicate the end of the reaction. The resulting dyestuff precipitates and can be filtered off and dried. It results a blue dyestuff powder, which is applied to cotton in one of the methods customary for reactive dyestuffs to produce brilliant strongly reddish bluish shades.

The dyestuff in form of the free acid has the following formula ( λ max: 572 nm)

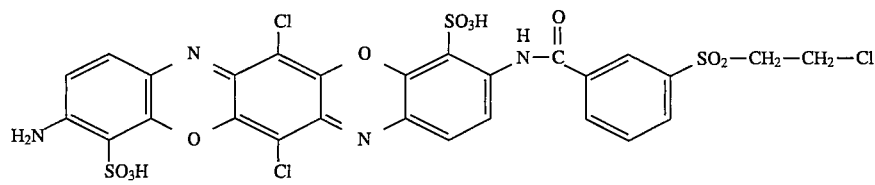

EXAMPLE 2

The vinyl form of the fiber-reactive triphenodioxazine dyestuff of Example 1 is obtained by adjusting the pH of the final reaction mixture to 11.5–12 at room temperature using

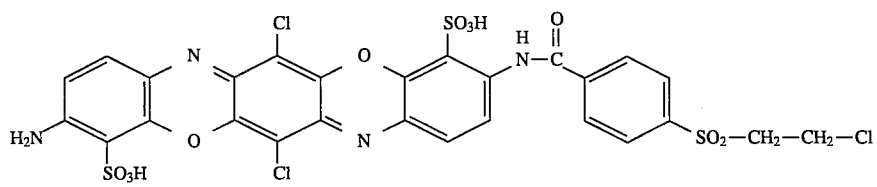

an aqueous solution of caustic soda. The mixture is held for 30 minutes at this pH, the pH is adjusted to 6 and the resulting dyestuff isolated.

The dyestuff in the free acid form has the following formula ($\lambda$ max: 585 nm):

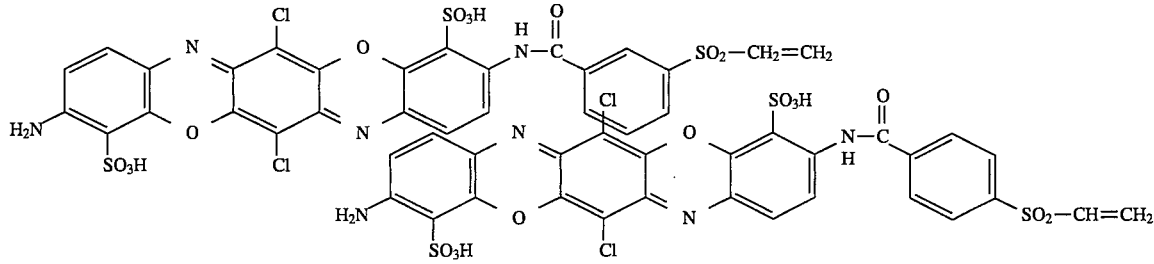

EXAMPLE 3

13.6 parts of 2,9-diamino-6,13-dichlorotriphenodioxazine-1,8-disulfonic acid is suspended in 200 parts of water and brought to pH 7.0 using an aqueous solution of 5% LiOH. The reaction mixture is stirred for one hour. The pH is adjusted with hydrochloric acid to pH 4.5 and 20 parts of 4-($\beta$-chloroethylsulfonyl)-benzoylchloride dissolved in 100 parts of methylene chloride is added over 2 hours. The pH of the reaction is maintained between 4–6 using an aqueous solution of 5% LiOH. After stirring for 6 hours at room temperature the reaction is completed. High performance liquid chromatography can be used to indicate the end of the reaction. The resulting dyestuff precipitates and can be filtered off and dried to provide a blue dyestuff powder. This dye may be applied to cotton one of the usual methods for reactive dyestuffs to produce a cotton substrate which is brilliant strongly reddish bluish shades.

The dyestuff in the free acid form has the following formula:

EXAMPLE 4

To prepare the vinyl form of the fiber-reactive triphenodioxazine dyestuff described under Example 3, the pH of the final reaction mixture is brought to 11.5–12 at room temperature by using an aqueous solution of caustic soda. After keeping the mixture for 30 minutes at this pH, the pH is brought back to 6 and the resulting dyestuff isolated.

The dyestuff in form of the free acid has the following formula:

Additional dyestuffs of the following general formula B' are obtained by using the procedure of the above examples. These products dye cotton in bright, strong reddish blue shades with good fastness properties.

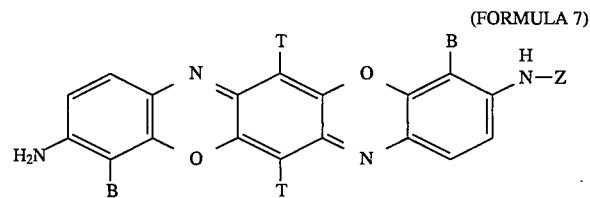

(FORMULA 7)

Examples 5–15c illustrate compounds of the general formula wherein substituents T, B and Z are as follows:

| Ex. | T | B | Z |
|---|---|---|---|
| 5 | Cl | SO₃H | −C(=O)−C₆H₄−CH₂−SO₂−CH₂−CH₂−Cl |
| 6 | Cl | SO₃H | −C(=O)−C₆H₄−CH₂−SO₂−CH=CH₂ |
| 7 | Cl | SO₃H | −C(=O)−C₆H₃(CH₃)−SO₂−CH₂−CH₂−Cl |
| 8 | Cl | SO₃H | −C(=O)−C₆H₂(CH₃)₂−SO₂−CH₂−CH₂−Cl (2,6-dimethyl) |
| 9 | Cl | SO₃H | −C(=O)−C₆H₂(CH₃)₂−SO₂−CH₂−CH₂−Cl (with two CH₃ groups and SO₂-CH₂-CH₂-Cl substituents) |
| 10 | Cl | SO₃H | −C(=O)−C₆H₄−CH₂−CH₂−SO₂−CH₂−CH₂−Cl |
| 11 | Br | SO₃H | −C(=O)−C₆H₄−SO₂−CH₂−CH₂−Cl |
| 12 | Br | SO₃H | −C(=O)−C₆H₄−SO₂−CH₂−CH₂−Cl |
| 13 | Cl | COOH | −C(=O)−C₆H₄−SO₂−CH₂−CH₂−Cl |
| 14 | Cl | COOH | −C(=O)−C₆H₄−SO₂−CH₂−CH₂−Cl |
| 15 | Cl | COOH | −C(=O)−C₆H₄−CH₂−SO₂−CH₂−CH₂−Cl |
| 15a | Cl | SO₃H | −C(=O)−C₆H₄−CH₂−SO₂−CVH₂−CH₂−Cl |

-continued

| Ex. | T | B | Z |
|---|---|---|---|
| 15b | Cl | COOH | ![structure] -C(=O)-C6H4-CH2-CH2-SO2-CH2-CH2-Cl |
| 15c | Cl | COOH | -C(=O)-C6H4-CH2-SO2-CVH2-CH2-Cl |

Additional dyestuffs of the following general formula C are obtained by using the procedure of the above examples. These products dye cotton in bright, strong reddish blue shades with good fastness properties.

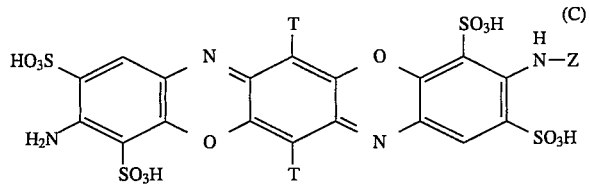

Examples 16–19 illustrate compounds of the general formula C wherein substituents T and Z are as follows:

| Ex. | T | Z |
|---|---|---|
| 16 | Cl | -C(=O)-C6H4-SO2-CH2-CH2-Cl |
| 17 | Cl | -C(=O)-C6H4-SO2-CH2-CH2-Cl |
| 18 | Cl | -C(=O)-C6H4-CH2-SO2-CH2-CH2-Cl |
| 19 | Br | -C(=O)-C6H4-SO2-CH2-CH2-Cl |

Dyes prepared according to the present invention are suitable for the dyeing of cellulosic materials such as cotton, linen, viscose, rayon or staple fibers. They can be applied by any one of the usual dyeing and printing methods for reactive dyestuffs and yield on cellulosic materials, in the presence of alkaline agents, brilliant shades having excellent fastness properties, and high color yield and reduced cold water bleeding. These dyes may also be used on wool, silk or polyamide fibers.

The invention may be embodied in other specific forms without departing from the spirit or essential characteristics thereof. Through this specification and the appended claims, a given chemical name or formula is intended to encompass all isomers of said name or formula where such isomers exist. The present embodiments are therefore to be considered in all respects as illustrative and not restrictive, the scope of the invention being indicated by the appended claims rather than by the foregoing description; and all changes which come within the meaning and equivalency of the claims are therefore intended to be embraced therein.

We claim:

1. A dye of the following formula:

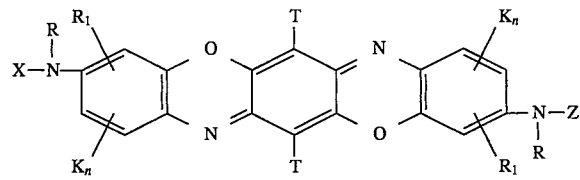

wherein:

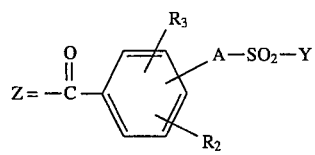

A is a covalent bond or a substituted or unsubstituted arylene, alkylene or arylene-alkylene group where the alkylene moiety may be optionally interrupted by a hereto atom;

Y is the vinyl group or the β-chloroethyl group and;

X is selected from H or Z;

K is independently selected from $SO_3H$ and COOH;

R and $R_1$ are independently selected from hydrogen and substituted or unsubstituted alkyl of 1 to 6 carbons;

$R_2$ and $R_3$ are independently selected from hydrogen and substituted or unsubstituted alkyl or alkoxy of 1 to 6 carbons;

T is independently selected from hydrogen, Cl, Br, a substituted or unsubstituted $C_1$ to $C_6$ alkyl, $C_1$ to $C_6$ alkoxy, phenyl or phenoxy; and n is independently selected from 0, 1 or 2.

2. A dyestuff according to claim 1 wherein T is Cl, n is 1, X is H or Z, K is $SO_3H$, or COOH, $R_1$ is H, R is H, and $R_2$ and $R_3$ are independently selected from H, $CH_3$ and $OCH_3$.

3. A dyestuff according to claim 1 having the following formula:

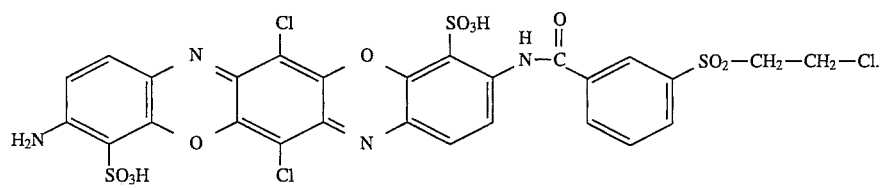
4. A dyestuff according to claim 1 having the following formula:
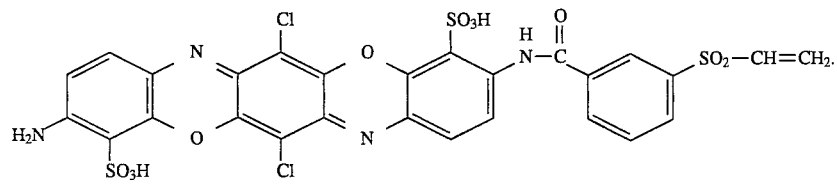
5. A dyestuff according to claim 1 having the following formula:
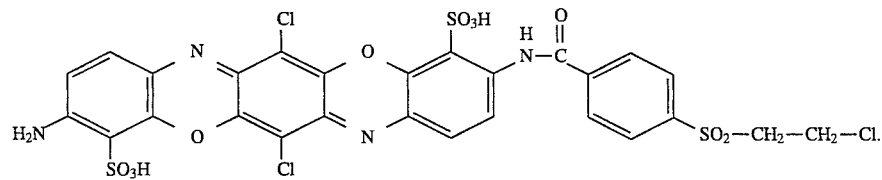
6. A dyestuff according to claim 1 having the following formula:
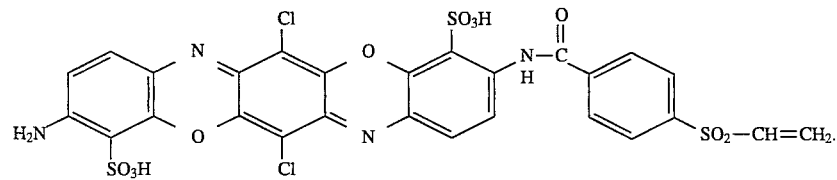
* * * * *